(12) United States Patent
Senn (10) Patent No.: US 11,391,614 B2
(45) Date of Patent: Jul. 19, 2022

(54) METERING CONTAINER FOR METERING VISCOUS MATERIAL COMPONENTS

(71) Applicant: Ivoclar Vivadent AG, Schaan (LI)

(72) Inventor: Bruno Senn, Gais (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 17/169,641

(22) Filed: Feb. 8, 2021

(65) Prior Publication Data

US 2021/0255016 A1    Aug. 19, 2021

(30) Foreign Application Priority Data

Feb. 19, 2020   (EP) ...................................... 20158251

(51) Int. Cl.
*G01F 11/02*    (2006.01)
*B65B 3/32*    (2006.01)

(52) U.S. Cl.
CPC .............. *G01F 11/021* (2013.01); *B65B 3/32* (2013.01)

(58) Field of Classification Search
CPC ............ A61B 17/0469; A61B 17/0482; A61B 17/0487; A61B 17/06061; A61B 17/06128; A61B 17/06161; A61B 17/06166; A61B 17/3421; A61B 2017/00362; A61B 2017/00867; A61B 2017/0472; A61B 2017/0479; A61B 2017/06142; A61B 2017/06176; A61C 5/60; A61C 5/62; A61C 5/64; A61C 5/68; A61M 2005/31598; A61M 5/007; A61M 5/16809; A61M 5/16827; A61M 5/1782; A61M 5/31511; A61M 5/31525; A61M 5/31555; A61M 5/31558; B65B 2220/14; B65B 29/10; B65B 3/003; B65B 3/12; B65B 3/32; G01F 11/021; A61J 1/22
See application file for complete search history.

(56) References Cited

U.S. PATENT DOCUMENTS

| 4,583,978 | A | | 4/1986 | Porat et al. | |
|---|---|---|---|---|---|
| 5,346,097 | A | * | 9/1994 | Melland | B65D 81/3288 222/132 |
| 6,464,107 | B1 | * | 10/2002 | Brugger | F04B 13/02 222/134 |
| 8,808,233 | B2 | | 8/2014 | Nelson et al. | |
| 9,346,069 | B2 | * | 5/2016 | Holzmann | B05B 11/3084 |

(Continued)

FOREIGN PATENT DOCUMENTS

| CN | 1065020 | A | * | 10/1992 | ............ A61M 5/315 |
|---|---|---|---|---|---|
| DE | 3102346 | C2 | * | 3/1989 | ............ G01F 11/025 |

(Continued)

*Primary Examiner* — Vishal Pancholi
*Assistant Examiner* — Bob Zadeh
(74) *Attorney, Agent, or Firm* — Ann M. Knab; Thad McMurray (57) ABSTRACT

The present invention relates to a metering container (100-1, 100-2) for metering a viscous material component (103-1, 103-2), comprising a piston (105-1, 105-2) for pressing the material component (103-1, 103-2) from a storage container (111-1, 111-2) into a metering chamber (107-1, 107-2); and a metering plunger (109-1, 109-2) for indicating a quantity of the material component (103-1, 103-2) in the metering chamber (107-1, 107-2), via which the material component (103-1, 103-2) can be dispensed from the metering chamber (107-1, 107-2).

13 Claims, 7 Drawing Sheets

(56) References Cited

U.S. PATENT DOCUMENTS

| | | | |
|---|---|---|---|
| 2001/0025860 A1* | 10/2001 | Auer | B05B 11/3029 |
| | | | 222/137 |
| 2011/0166531 A1 | 7/2011 | Stroumpoulis et al. | |
| 2011/0184348 A1* | 7/2011 | Bates | A61M 5/14244 |
| | | | 604/131 |
| 2012/0215205 A1* | 8/2012 | Alvey | A61J 1/2093 |
| | | | 604/516 |
| 2019/0255250 A1 | 8/2019 | Bates et al. | |
| 2021/0255016 A1* | 8/2021 | Senn | A61C 5/60 |

FOREIGN PATENT DOCUMENTS

| | | | |
|---|---|---|---|
| FR | 2692040 A1 * | 12/1993 | B05B 11/307 |
| NL | 1033672 C2 * | 10/2007 | H01M 10/4242 |

* cited by examiner

METERING CONTAINER FOR METERING VISCOUS MATERIAL COMPONENTS

CROSS-REFERENCE TO RELATED APPLICATIONS

This application claims priority to European patent application No. 20158251.7 filed on Feb. 19, 2020, the disclosure of which is incorporated herein by reference in its entirety.

FIELD OF THE INVENTION

The present invention relates to a metering container for metering a viscous material component, a metering system comprising a first and a second metering container and a method for metering viscous material components.

BACKGROUND

Inaccuracies can result during the metering of viscous material components. The manual metering of viscous material components is time-intensive and inaccurate.

U.S. Pat. Nos. 4,583,978, 8,808,233, 20120215205, 20110166531, and 20190255250 are directed to dispensing devices and are hereby incorporated by reference in their entirety.

SUMMARY

It is an object of the present invention to simplify and accelerate the metering of viscous material components.

This technical object is achieved by subject-matter comprising the features according to the independent claims. Advantageous embodiments are subject to the dependent claims, the description and the drawings.

According to a first aspect, the technical object is achieved by a metering container for metering a viscous material component, comprising a piston for pressing the material component from a storage container into a metering chamber; and a metering plunger for indicating a quantity of the material component in the metering chamber, via which the material component can be dispensed from the metering chamber. The metering container provides the technical advantage that the quantity of material component to be dispensed can be accurately determined by the metering plunger.

In a technically advantageous embodiment of the metering container, the storage container and/or the metering chamber are cylindrical. This provides for example the technical advantage that the piston and/or the metering plunger can be produced in a simple manner.

In a further technically advantageous embodiment of the metering container, the metering container comprises an intermediate closing device for closing a connection channel between the storage container and the metering chamber. This provides for example the technical advantage that unintentional mixing of different material components can be prevented.

In a further technically advantageous embodiment of the metering container, the metering container comprises a dispensing-closing device for closing a dispensing opening for the material component. This provides for example the technical advantage that unintentional dispensing of the material component can be prevented.

In a further technically advantageous embodiment of the metering container, the metering container comprises a metering chamber for a further material component. This provides for example the technical advantage that two material components can be dispensed by the same metering container.

According to a first aspect, the technical object is achieved by a metering system comprising a first metering container according to the first aspect and a second metering container, wherein the metering plunger for the material component of the first metering container and the metering plunger for the material component of the second metering container are mechanically connected to one another. The metering system provides for example the technical advantage that the two material components can be dispensed at the same time with one movement.

In a technically advantageous embodiment of the metering system, the piston of the first metering container and the piston of the second metering container are arranged in parallel with one another. This provides for example the technical advantage that two pistons can be actuated at the same time by the same move.

In a further technically advantageous embodiment of the metering system, the metering system comprises a metering nozzle having a first channel for the material component of the first metering container and a second channel for the material component of the second metering container. This provides for example the technical advantage that the two material components can be dispensed separately by the metering system.

In a further technically advantageous embodiment of the metering system, the metering nozzle forms an intermediate closing device and/or dispensing-closing device of the first metering container and of the second metering container. The metering nozzle can be movable for example between a first position for closing the connection channel and a second position for closing the dispensing opening. This provides for example the technical advantage that the dispensing opening and the connection channel can be closed and opened in a simple manner in terms of fluid technology.

In a further technically advantageous embodiment of the metering system, the metering plunger for the first material component has a length such that it extends to the end of the first channel and/or the metering plunger for the second material component has a length such that it extends to the end of the second channel. This provides for example the technical advantage that the metered material components can be dispensed completely from the metering system.

In a further technically advantageous embodiment of the metering system, the metering system comprises a mixing container for receiving the first and the second material component. This provides for example the technical advantage that the two material components can be mixed internally.

In a further technically advantageous embodiment of the metering system, the mixing container can be plugged onto the metering nozzle. This provides for example the technical advantage that the mixed material components can be removed from the metering system in a simple manner.

In a further technically advantageous embodiment of the metering system, the mixing container can be displaced on the metering nozzle by reason of the ingress of the first and second material component. This provides for example the technical advantage that the introduction and mixing of the material components can be performed without the ingress of air.

In a further technically advantageous embodiment of the metering system, the first metering container and the second metering container can be separated from one another. This provides for example the technical advantage that different material components can be combined and mixed with one another.

According to a third aspect, the technical object is achieved by a method for metering viscous material components, comprising the steps of pressing the material component from a storage container into a metering chamber; and dispensing the material component from the metering chamber by means of a metering plunger. The method provides the same technical advantages as the metering container according to the first aspect.

BRIEF DESCRIPTION OF THE DRAWINGS

Exemplified embodiments of the invention are illustrated in the drawings and are described in more detail hereinunder.

In the drawings.

DETAILED DESCRIPTION

Figure 1A:
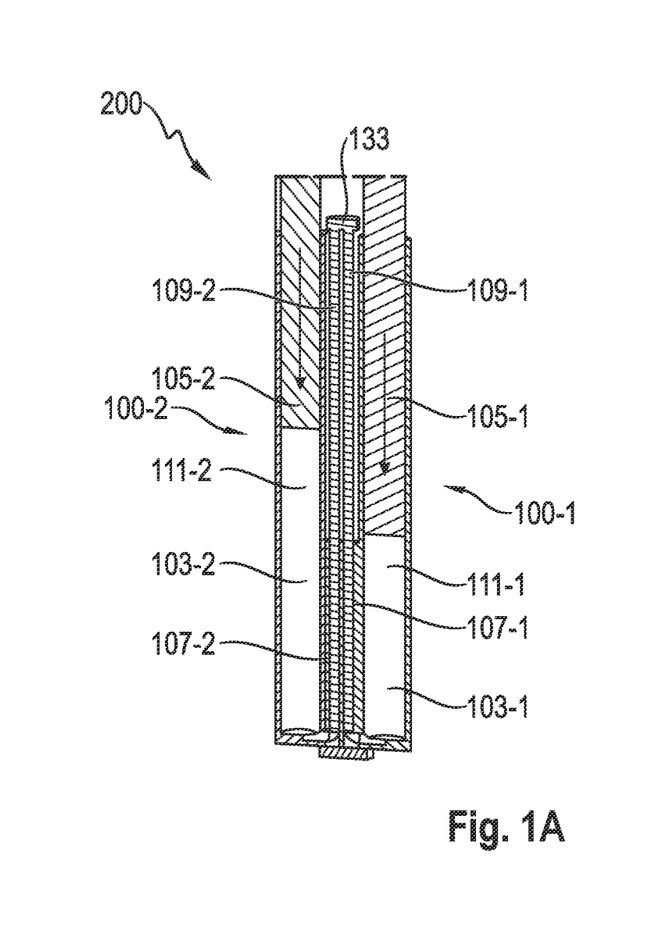
FIG. 1A shows a cross-sectional view of a metering system comprising a first and a second metering container.
Figure 1B:
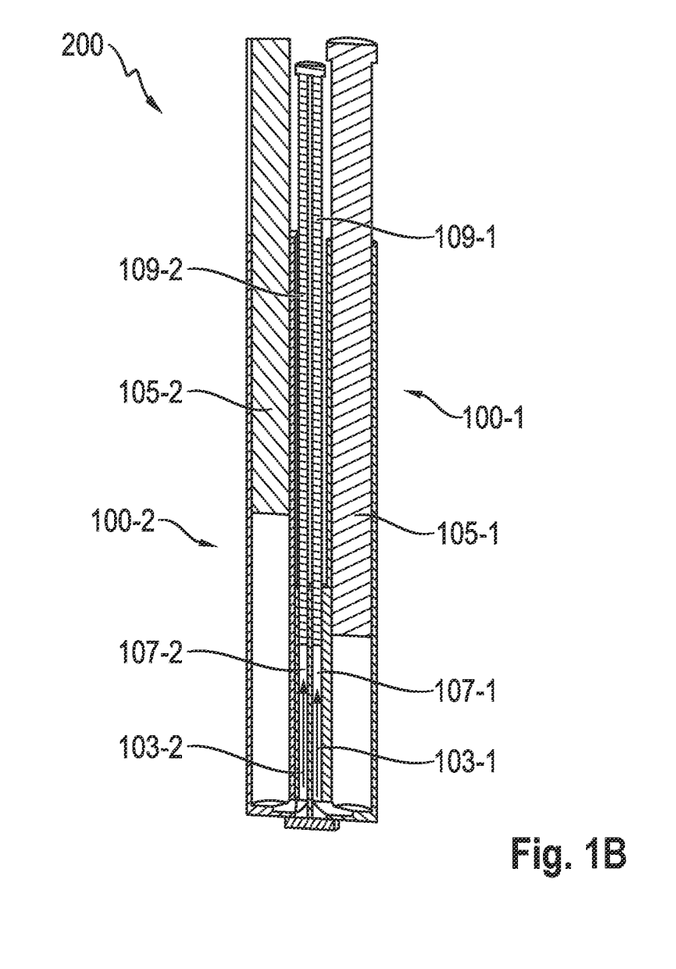
FIG. 1B shows a cross-sectional view of a metering system comprising a first and a second metering container.

FIGS. 1A and 1B show a cross-sectional view of a metering system 200 comprising a first and a second metering container 100-1 and 100-2. The first metering container 100-1 comprises a cylindrical storage container 111-1, in which a first viscous material component 103-1 is located. This material component 103-1 is for example a viscous dental synthetic material composition consisting of a viscous material for a dental filling or dental formulation which is subsequently cured. The material component 103-1 has a viscosity of 3000-50000 Pas. However, in general it is also possible to use other viscous material components 103-1 which are suitable for the metering system.

By pressing a piston 105-1 in the direction of the arrow, the viscous material component 103-1 is pressed from the storage container 111-1 into a cylindrical metering chamber 107-1. During this procedure, the metering plunger 109-1 moves in an opposite direction. This minimises the trapped air in the metering chamber 107-1. With the aid of the stroke of the metering plunger 109-1, the quantity and the volume of the material component 103-1 located in the metering chamber 107-1 can be determined. Since the metering chamber 107-1 has a smaller diameter than the storage container 111-1, the quantity of the material component 103-1 in the metering chamber 107-1 can be determined with a high level of accuracy.

If the metering plunger 109-1 is subsequently moved in the other direction, the material component 103-1 located in the metering chamber 107-1 is dispensed, in turn, from the metering chamber 107-1 of the metering system 200.

In addition, the metering container 100-1 comprises a second metering chamber 107-2 for a further material component 103-2 from another storage container 111-2. This material component 103-2 is for example a viscous dental material component consisting of a viscous synthetic material for a dental filling or dental formulation which is used for colouring or curing purposes. The material component 103-2 has a viscosity of 3000-50000 Pas. However, in general it is also possible to use other viscous material components 103-2 which are suitable for the metering system.

The material components 103-1 or 103-2 have for example a density of approximately 2.1 g/cm$^3$. The quantity of the material components 103-1 or 103-2 for each storage container 111-1 or 111-2 can be approximately 10 g or up to 20 or 30 g or in a range of 5-40 g. The metering quantity for each material component 103-1 or 103-2 can be 0.15 g to 0.5 g. However, in general other values can also be selected in this case.

This storage container 111-2 is coupled to the storage container 111-1 in terms of fluid technology such that the material component 103-2 can flow from the storage container 111-2 into the other metering chamber 107-2. This occurs by pressing the second piston 105-2, which is arranged in parallel with the first piston 105-1, in the direction of the arrow. In so doing, the second metering plunger 109-2 likewise moves in the opposite direction and thereby indicates the quantity of the material component 103-2 located in the metering chamber 107-2. This material component 103-2 can then also be dispensed from the metering chamber 107-2 by means of the second metering plunger 109-2.

The metering plungers 109-1 and 109-2 arranged in parallel can be coupled or connected mechanically to one another by means of a crosspiece 133 and so they can be moved together. The metering containers 100-1 and 100-2 and the remaining parts are formed for example by means of corresponding moulded parts from synthetic material. By means of the metering system 200, the accuracy of the metering is independent of the compression behaviour of the material component 103-1 and 103-1. The metering system 200 has a small dead volume and so a small amount of residual material remains in the metering containers 100-1 and 100-2.

Figure 2A:
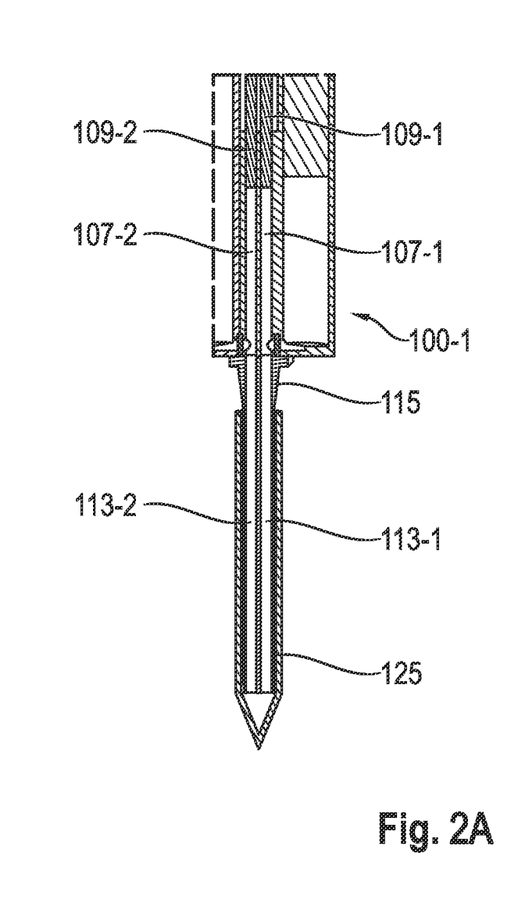
FIG. 2A shows a cross-sectional view of the metering system comprising a metering nozzle.
Figure 2B:
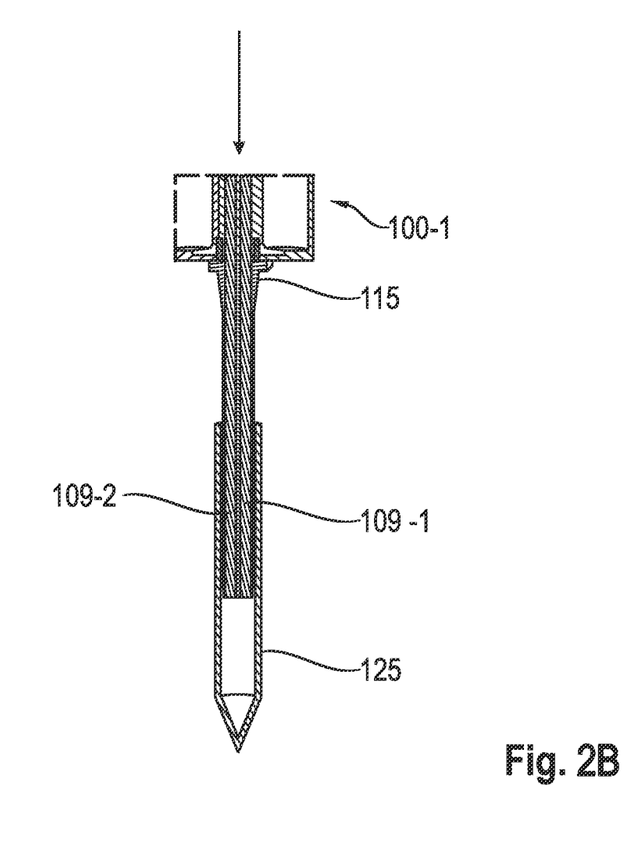
FIG. 2B shows a cross-sectional view of the metering system comprising a metering nozzle.

FIGS. 2A and 2B show a cross-sectional view of the metering system 200 comprising a metering nozzle 115. The metering nozzle 115 is formed for example by means of a synthetic material part, in which a first channel 113-1 is formed for the material component 103-1 and a second channel 113-2 is formed for the material component 103-2. The first and the second channel 113-1 and 113-2 each have the same diameter as the respective metering chamber 107-1 and 107-2.

The length of the metering plungers 109-1 and 109-2 is selected such that they can press the material component 103-1 and 103-2 completely out of the channels 113-1 and 113-2. In this way, the material components 103-1 and 103-2 can be released completely from the metering chambers 107-1 and 107-2 and from the metering system 200.

The lower end of the metering nozzle 115 can have a mixing container 125 attached to it which serves to receive the first and the second material component 103-1 and 103-2. When the material components 103-1 and 103-2 are being dispensed from the metering system 200, the displaceable mixing container 125 slides along the metering nozzle 115. In this manner, the material components 103-1 and 103-2 can be mixed in the mixing container 125 without the ingress of air into the mixing container 125.

Figure 3:
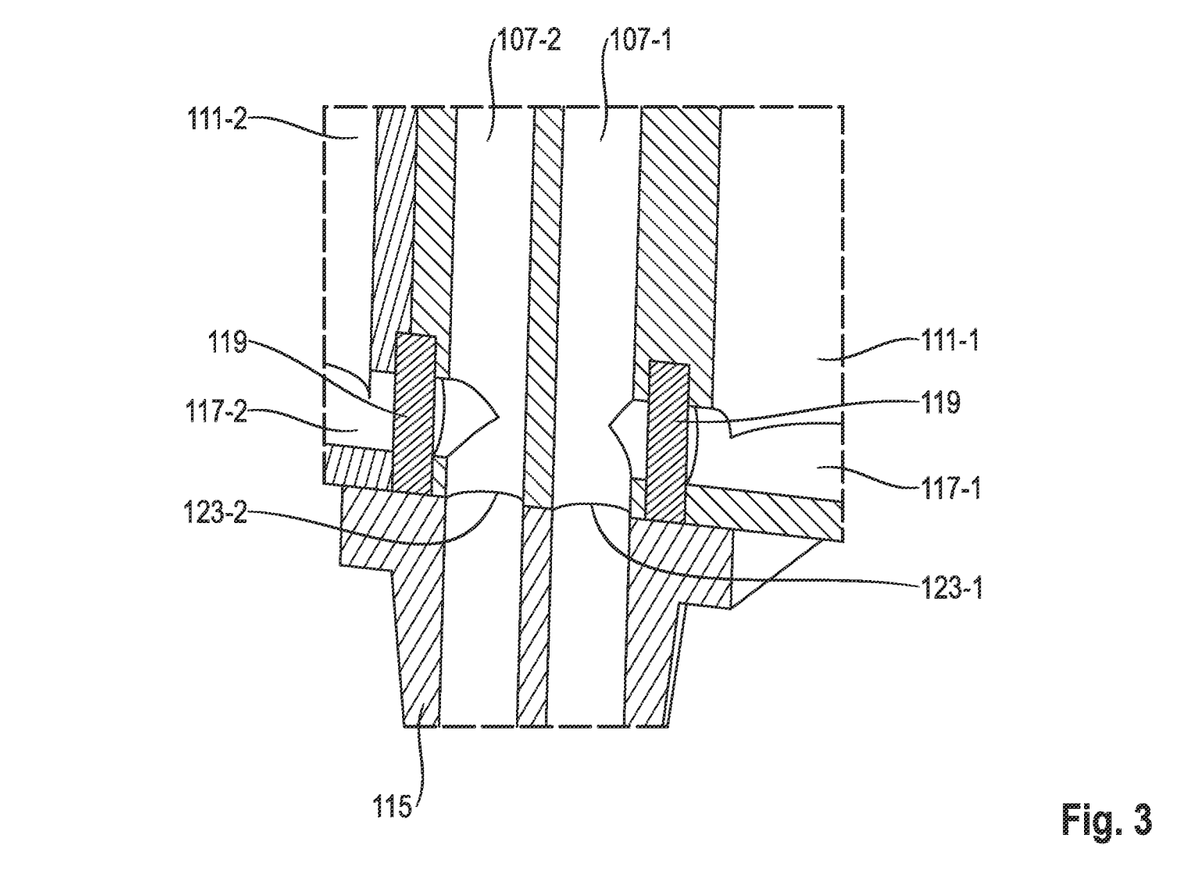
FIG. 3 shows a cross-sectional view of the metering system comprising an intermediate closing device.

FIG. 3 shows a cross-sectional view of the metering system 200 comprising an intermediate closing device 119. The intermediate closing device 119 serves to close a connection channel 117-1 and 117-2 which extends between the storage container 111-1 or 111-2 and the metering chamber 107-1 or 107-2. The viscous material component 103-1 and 103-2 flows through the connection channel 117-1 and 117-2 out of the respective storage containers 111-1 and 111-2 into the metering chambers 107-1 and 107-2. A flow of the material components 103-1 and 103-2 can be selectively stopped by the intermediate closing device 119. For this purpose, the intermediate closing device 119 can be moved between different positions.

The intermediate storage device 119 can be coupled, for example, mechanically to the movable metering nozzle 115. If the metering nozzle 115 is moved to a specific position, the connection channels 117-1 and 117-2 can be closed. This can prevent the material components 103-1 and 103-2 from flowing back into the storage containers 111-1 and 111-2 as they are being pressed out.

The intermediate closing device 119 can be formed for example by means of a movable disk which is moved into the respective connection channel 117-1 and 117-2. However, the intermediate closing device 119 can also comprise a non-return valve which prevents the back-flow of the material components 103-1 or 103-2 into the storage containers 111-1 and 111-2. The dispensing openings 123-1 and 123-2 are opened for dispensing the two material components 103-1 and 103-2 so that the material components can flow through the two channels 113-1 and 113-2 of the metering nozzle 115.

Figure 4A:
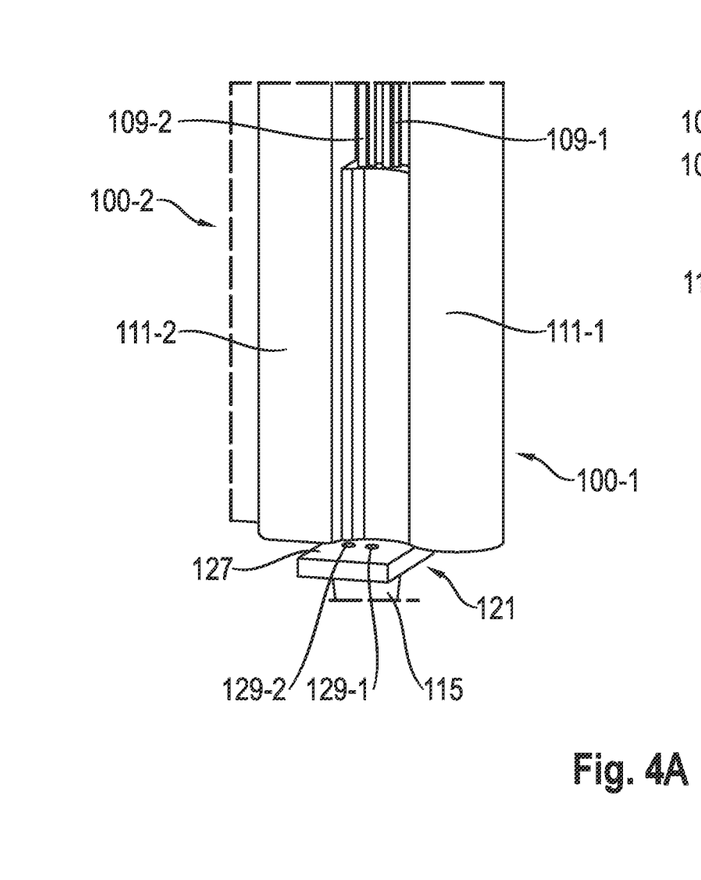
FIG. 4A shows an external view of the metering system comprising a displaceable metering nozzle.
Figure 4B:
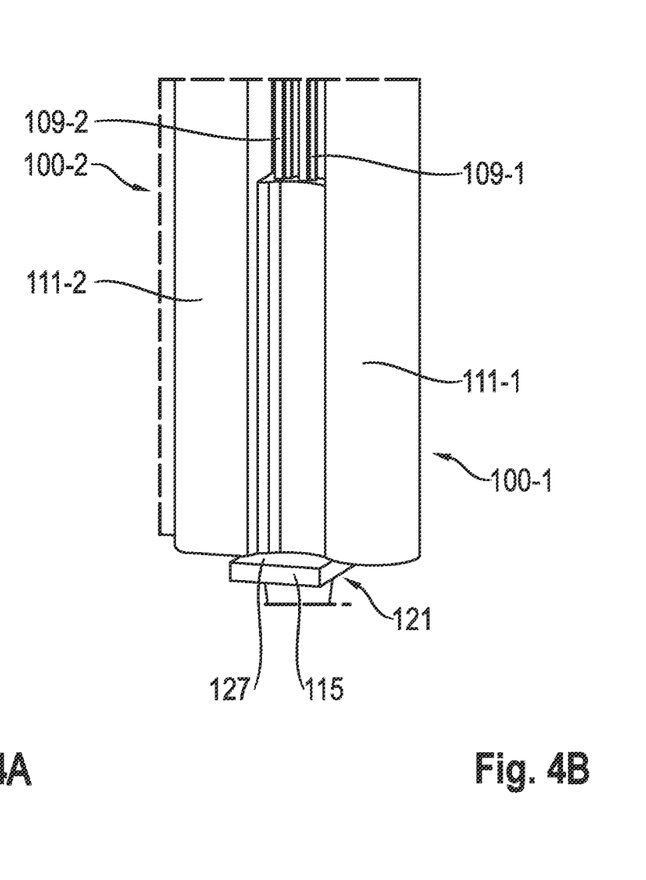
FIG. 4B shows an external view of the metering system comprising a displaceable metering nozzle.

FIGS. 4A and 4B show an external view of the metering system 200 comprising a displaceable metering nozzle 115. The displaceable metering nozzle 115 comprises an adjoining plate 127, in which two through-openings 129-1 and 129-2 are formed. As a result, a dispensing-closing device 121 is formed. In the first position of the plate 127, its closed surface is located in front of the dispensing openings 123-1 and 123-2 of the metering chambers 107-1 or 107-2, thus preventing the material components 103-1 and 103-2 from being output from the metering chambers 107-1 or 107-2. In this position, the connection channels 117-1 and 117-2 in the interior of the metering system 200 are open.

The metering nozzle 115 can be moved linearly to the side. Then, the plate 127 is located in a second position, in which the respective through-openings 129-1 and 129-2 and the dispensing openings 123-1 and 123-2 lie one over the other so that the material components 103-1 and 103-2 can be dispensed from the metering chambers 107-1 or 107-2. The closed dispensing-openings 123-1 and 123-2 of the metering chambers 107-2 thus become open with respect to the metering nozzle 115. In this position, the connection channels 117-1 and 117-2 in the interior of the metering system 200 are closed.

Figure 5:
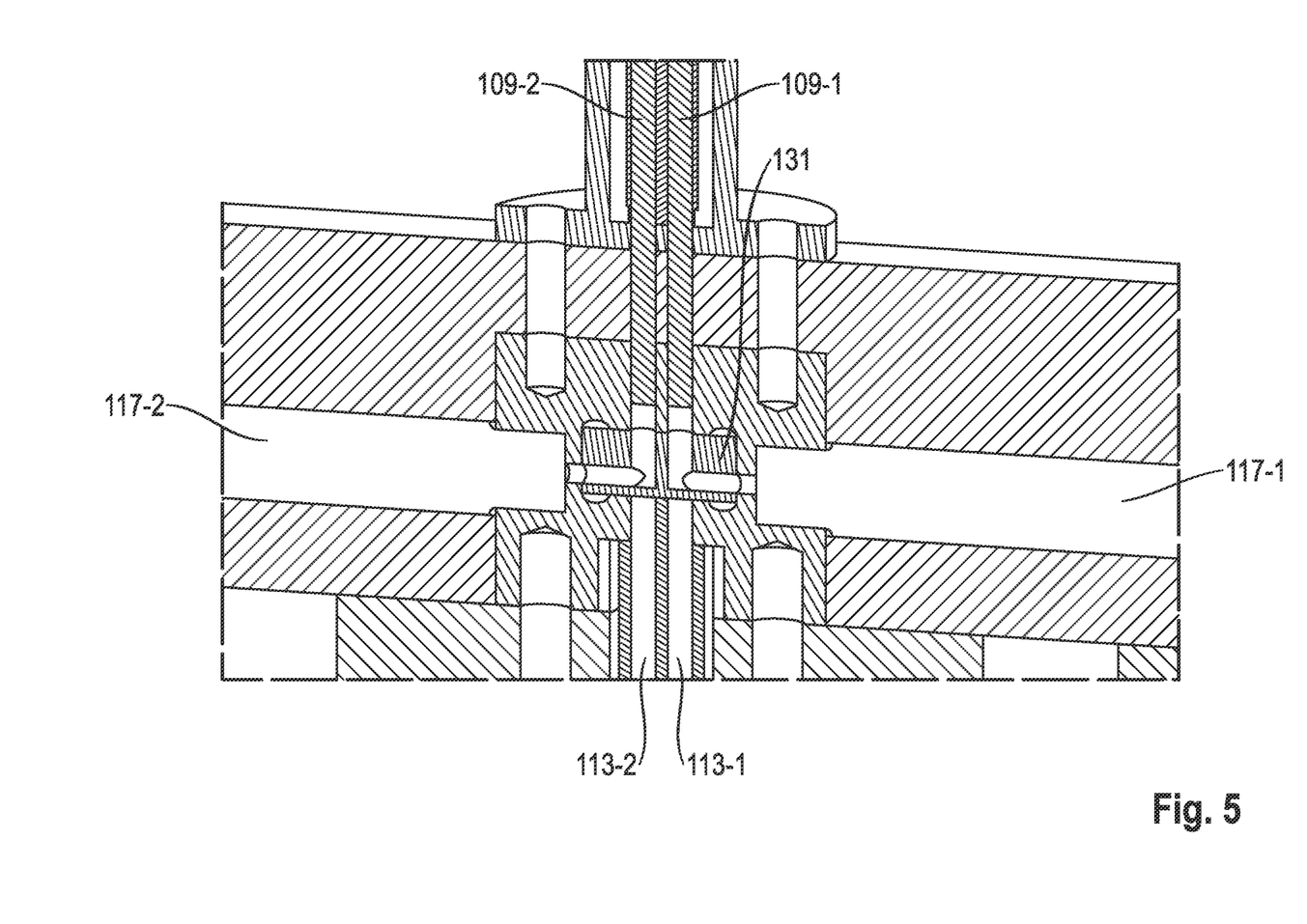
FIG. 5 shows a cross-sectional view of an intermediate closing device and a dispensing closing device in a first position.

FIG. 5 shows a cross-sectional view of an intermediate closing device 119 and a dispensing-closing device 121 in a first position. In this case, both the intermediate closing device 119 as well as the dispensing-closing device 121 are formed by a common sliding part 131. In the position shown, the sliding part 131 opens the connection channels 117-1 and 117-2 in the interior of the metering system 200 so that material components 103-1 and 103-2 can be pressed therethrough from the storage containers 111-1 and 111-2 into the metering chambers 107-1 or 107-2. However, the dispensing openings 123-1 and 123-2 are closed by the sliding part 131, thus preventing the material components 103-1 and 103-2 from being output.

Figure 6:
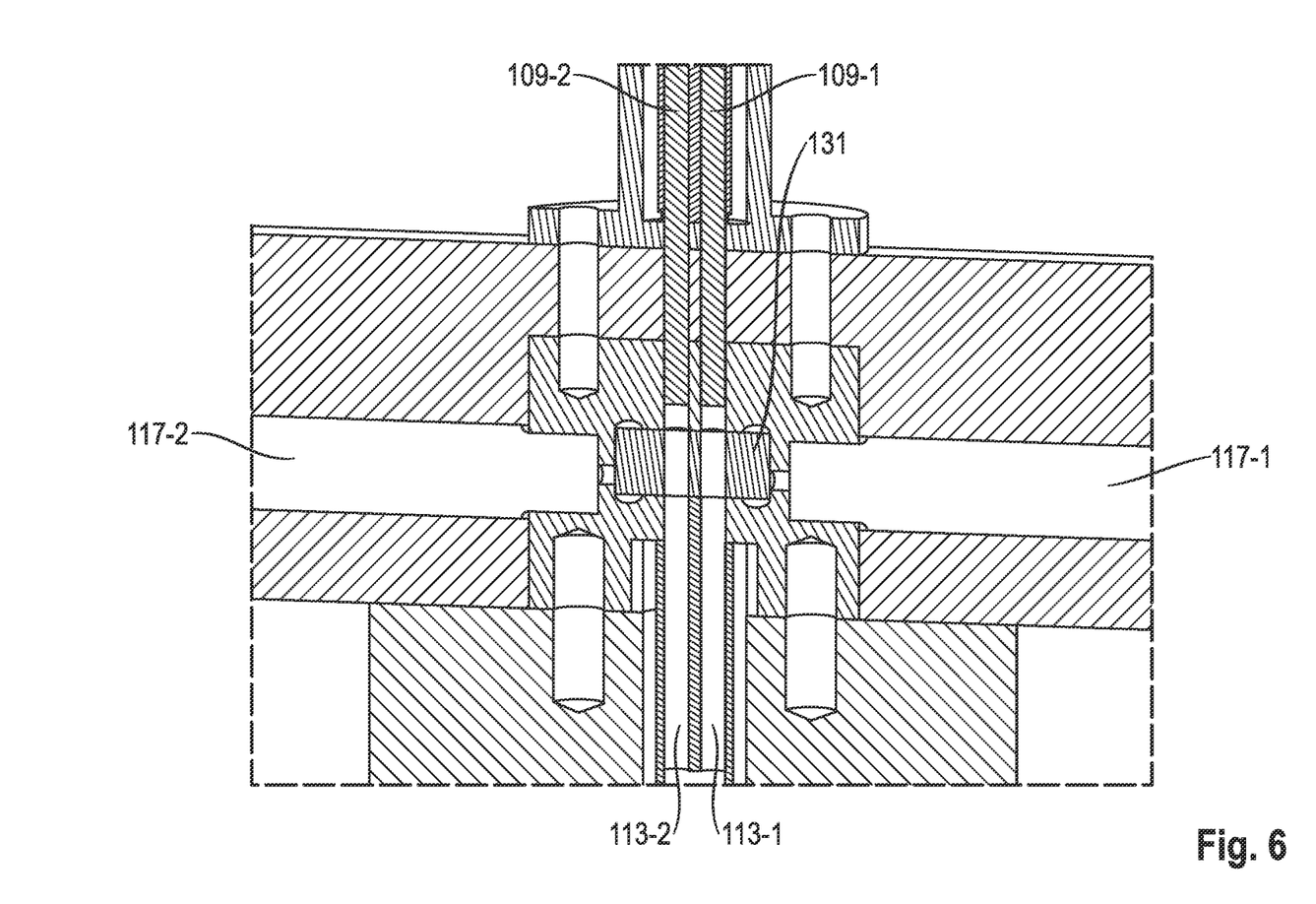
FIG. 6 shows a cross-sectional view of the intermediate closing device and dispensing closing device in a second position.

FIG. 6 shows a cross-sectional view of the intermediate closing device 119 and a dispensing-closing device 121 in a second position. In this position, the sliding part 131 opens the dispensing openings 123-1 and 123-2 and so the material components 103-1 and 103-2 can be dispensed from the metering chambers 107-1 or 107-2 into the channels 113-1 and 113-2 of the metering nozzle 115. However, the connection channels 117-1 and 117-2 in the interior are closed by the sliding part 131 so that back-flow of the material components 103-1 and 103-2 into the metering chambers 107-1 or 107-2 is prevented.

Figure 7:
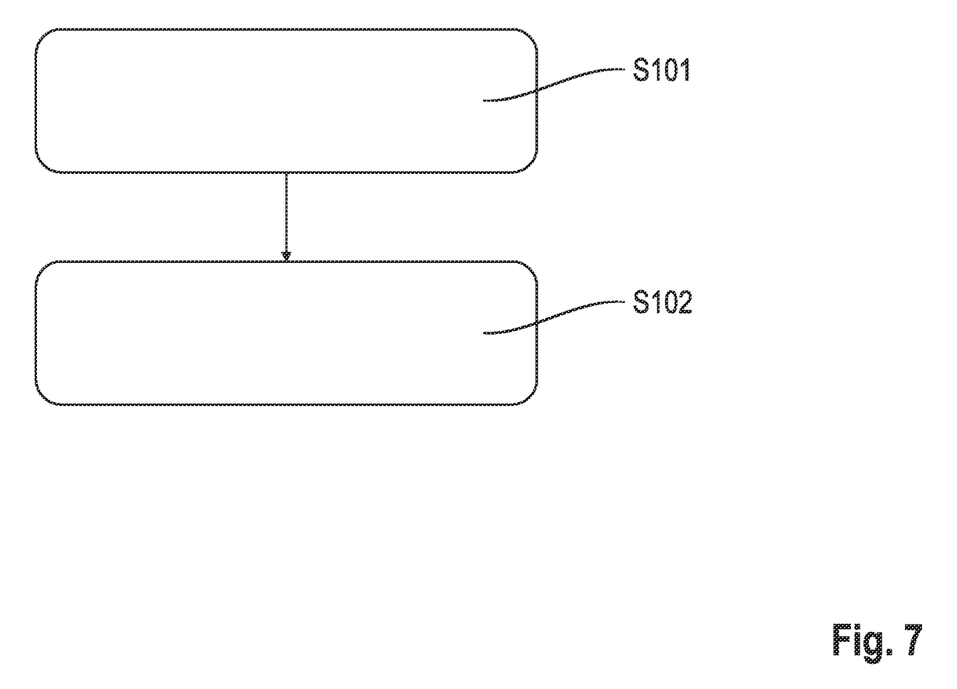
FIG. 7 shows a block diagram of a method for metering viscous material components.

FIG. 7 shows a block diagram of a method for metering viscous material components 103-1 and 103-2. In a first step, the material component 103-1 or 103-2 is pressed from the storage container 111-1 or 111-2 by the pistons 105-1 and 105-2 into the metering chamber 107-1 or 107-2. The ingress of the material component 103-1 and 103-2 causes the metering plunger 109-1 or 109-2 to move out of the metering chamber 107-1 or 107-2. Then, the intermediate closing device 119 and the dispensing-closing device 121 are switched.

Subsequently, in step S102 the material component 103-1 or 103-2 is completely dispensed from the metering chamber 107-1 or 107-2 via the metering plunger 109-1 or 109-2. This occurs by means of moving the metering plunger 109-1 or 109-2 in the opposite direction. This method can also be performed with coupled metering containers 100-1 and 100-2. The two metering plungers 109-1 or 109-2 can be moved at the same time and so both material components 103-1 or 103-2 can be dispensed from the metering system 200 at the same time.

By reason of the method, the accuracy of the metering is independent of the compression behaviour of the material components 103-1 and 103-2. A small dead volume is produced and so a small amount of residual material remains in the metering system 200.

All features explained and illustrated in conjunction with individual embodiments of the invention can be provided in a different combination in the subject-matter in accordance with the invention in order to achieve the advantageous effects thereof at the same time.

All the method steps can be implemented by apparatuses which are suitable for carrying out the respective method step. All functions which are carried out by features relating to the apparatus can be a method step of a method.

The scope of protection of the present invention is set by the claims and is not limited by the features explained in the description or shown in the figures.

LIST OF REFERENCE SIGNS 100 metering container
103 material component
105 piston
107 metering chamber
109 metering plunger
111 storage container
113 channel
115 metering nozzle
117 connection channel
119 intermediate closing device
121 dispensing-closing device 123 dispensing opening
125 mixing container
127 plate
129 through-openings
131 sliding part
133 crosspiece

The invention claimed is:

1. Metering container (100-1, 100-2) for metering a viscous material component (103-1, 103-2), comprising: a piston (105-1, 105-2) for pressing the material component (103-1, 103-2) from a storage container (111-1, 111-2) into a metering chamber (107-1, 107-2); and a metering plunger (109-1, 109-2) for indicating a quantity of the material component (103-1, 103-2) in the metering chamber (107-1, 107-2), via which the material component (103-1, 103-2) can be dispensed from the metering chamber (107-1, 107-2); and the metering system (200) comprises a metering nozzle (115) attached to the metering container (100-1, 100-2), the metering nozzle (115) having a channel (113-1, 113-2) for the material component (103-1, 103-2) of the metering container (100-1, 100-2), wherein the metering plunger (109-1, 109-2) for the material component (103-1, 103-2) has a length such that it extends to an end of the channel (113-1, 113-2).

2. Metering container (100-1, 100-2) as claimed in claim 1, wherein the storage container (111-1, 111-2) and/or the metering chamber (107-1) are cylindrical.

3. Metering container (100-1, 100-2) as claimed in claim 1, wherein the metering container (100-1, 100-2) comprises an intermediate closing device (119) for closing a connection channel (117-1, 117-2) between the storage container (111-1, 111-2) and the metering chamber (107-1, 107-2).

4. Metering container (100-1, 100-2) as claimed in claim 1, wherein the metering container (100-1, 100-2) comprises a dispensing-closing device (121) for closing a dispensing opening (123-1, 123-2) for the material component (103-1, 103-2).

5. Metering container (100-1, 100-2) as claimed in claim 1, wherein the metering container (100-1, 100-2) comprises a second metering chamber (107-2) for a further material component (103-2).

6. Metering system (200) for metering a viscous material component comprising a first metering container (100-1) and a second metering container (100-2), a piston (105-1, 105-2) for pressing the material component (103-1, 103-2) from a storage container (111-1, 111-2) into a metering chamber (107-1, 107-2); and a first and second metering plunger (109-1, 109-2) for indicating a quantity of the material component (103-1, 103-2) in the metering chamber (107-1, 107-2), via which the material component (103-1, 103-2) can be dispensed from the metering chamber (107-1, 107-2), wherein the first metering plunger (109-1) for the material component (103-1) of the first metering container (100-1) and the second metering plunger (109-2) for the material component (103-2) of the second metering container (100-2) are mechanically connected to one another; and the metering system (200) comprises a metering nozzle (115) attached to the first and second metering containers (100-1, 100-2), the metering nozzle (115) having a first channel (113-1) for the material component (103-1) of the first metering container (100-1) and a second channel (113-2) for the material component (103-2) of the second metering container (100-1), wherein the metering plunger (109-1) for the first material component (103-1) has a length such that it extends to an end of the first channel (113-1) and/or the metering plunger (109-2) for the second material component (103-2) has a length such that it extends to an end of the second channel (113-2).

7. Metering system (200) as claimed in claim 6, wherein the piston comprises first and second pistons, wherein the first piston (105-1) of the first metering container (100-1) and the second piston (105-2) of the second metering container (100-2) are arranged in parallel with one another.

8. Metering system (200) as claimed in claim 6, wherein the metering nozzle (115) forms an intermediate closing device (119) and/or dispensing-closing device (121) of the first metering container (100-1) and of the second metering container (100-2).

9. Metering system (200) as claimed in claim 6, wherein the metering system (200) comprises a mixing container (125) for receiving the first and the second material component (103-1, 103-2).

10. Metering system (200) as claimed in claim 9, wherein the mixing container (125) can be plugged onto the metering nozzle (115).

11. Metering system (200) as claimed in claim 10, wherein the mixing container (125) can be displaced on the metering nozzle (115) by reason of the ingress of the first and second material component (103-1, 103-2).

12. Metering system (200) as claimed in claim 6, wherein the first metering container (100-1) and the second metering container (100-2) can be separated from one another.

13. Method for metering viscous material components (103-1, 103-2), comprising the steps of: pressing (3101) the material component (103-1, 103-2) from a storage container (111-1, 111-2) into a metering chamber (107-1, 107-2); indicating a quantity of the material component (103-1, 103-2) in the metering chamber (107-1, 107-2) by a metering plunger (109-1, 109-2); and dispensing (3102) the material component (103-1, 103-2) from the metering chamber (107-1, 107-2) via a metering plunger (109-1, 109-2); and a metering nozzle (115) attached to the storage container (111-1, 111-2), the metering nozzle (115) having a channel (113-1, 113-2) for the material component (103-1, 103-2) of the metering container (100-1, 100-2), wherein the metering plunger (109-1, 109-2) for the material component (103-1, 103-2) has a length such that it extends to an end of the channel (113-1, 113-2).

* * * * *